(12) United States Patent
Fujita et al.

(10) Patent No.: US 10,775,560 B1
(45) Date of Patent: Sep. 15, 2020

(54) OPTICAL SENSING AND PHOTOCATALYSIS DEVICES BASED ON THREE-DIMENSIONAL WAVEGUIDING STRUCTURES AND METHOD OF USING SAME

(71) Applicant: SCIDATEK INC., Austin, TX (US)

(72) Inventors: Junichiro Fujita, Los Altos, CA (US); Louay Eldada, Austin, TX (US)

(73) Assignee: SCIDATEK INC., Austin, TX (US)

( * ) Notice: Subject to any disclaimer, the term of this patent is extended or adjusted under 35 U.S.C. 154(b) by 0 days.

(21) Appl. No.: 16/919,549

(22) Filed: Jul. 2, 2020

(51) Int. Cl.
*G02B 6/13* (2006.01)
*G02B 6/12* (2006.01)

(52) U.S. Cl.
CPC ...................... *G02B 6/12* (2013.01)

(58) Field of Classification Search
CPC ........ G02B 6/1225; G02B 2006/12061; G02B 6/1228; G02B 6/34; G02B 6/124; G02B 2006/12097; G02B 6/12007; G02B 2006/12104; G02B 6/43; G02B 2006/12038; G02B 2006/12107; G02B 2006/12114; G02B 2006/12135; G02B 2006/12161; G02B 2006/12164; G02B 2006/12176; G02B 27/285; G02B 5/045; G02B 6/10; G02B 6/12004; G02B 6/12026; G02B 6/12033; G02B 6/2861; G02B 6/4232; G02B 6/12011; G02B 6/29349; G02B 6/29358; G02B 6/4215; G02B 6/125; G02B 6/13; G02B 6/12002; (Continued)

(56) References Cited

U.S. PATENT DOCUMENTS 5,444,249 A 8/1995 Wong
5,747,808 A 5/1998 Wong
(Continued)

OTHER PUBLICATIONS

K. Imamura et al, "Investigation on multi-core fibers with large Aeff and low micro bending loss," Optics Express, vol. 19, No. 11, pp. 10595-10603 (2011).
(Continued)

*Primary Examiner* — Michael P Stafira
(74) *Attorney, Agent, or Firm* — Pierson Intellectual Property LLC

(57) ABSTRACT

Small form-factor, sensitive and efficient waveguide devices capable of nondispersive infrared gas or liquid sensing and photocatalysis are designed based on photonic integrated circuits. The devices comprise three-dimensional optical waveguiding structures and preferably integrated light sources and photodetectors.
Since the length of the waveguide scales with the number of waveguiding layers, a plurality of layers is used to design high-sensitivity sensors and high-efficiency photocatalysis devices.
In one embodiment, titanium dioxide absorbs ultraviolet light to generate an electron-hole pair which, in the presence of water and oxygen, generates radicals that react with and mineralize undesirable organic compounds, such as the lipid membranes that envelope and protect viruses such as Coronavirus Disease 2019 (COVID-19), allowing to pry apart the membranes and destroy the cells. Such photocatalysis devices can be used in airflow systems designed to circulate the air of essentially confined spaces through these devices to create air-disinfecting systems.

21 Claims, 7 Drawing Sheets

(58) Field of Classification Search
CPC .... G02B 6/1221; G02B 6/305; G02B 6/3504; G02B 6/3596; G02B 6/06; G02B 6/122; G02B 6/136; G02B 6/2931; G02B 2006/1215; G02B 6/126; G02B 6/138; G02B 6/262; G02B 6/29331; G02B 6/2934; G02B 6/29395; G02B 6/3534; G02B 6/4214; G02B 2006/0325; G02B 6/1223; G02B 6/29308; G02B 6/29313; G02B 6/29314; G02B 6/29389; G02B 6/30; G02B 6/3508; G02B 6/4239; G02B 2006/12095; G02B 2006/12119; G02B 2006/12142; G02B 2006/12147; G02B 27/1086; G02B 27/144; G02B 27/145; G02B 6/08; G02B 6/132; G02B 6/2804; G02B 6/29328; G02B 6/2938; G02B 6/3838; G02B 6/3845; G02B 6/3885; G02B 6/4212; G02B 6/4231; G02B 2006/12138; G02B 2006/12152; G02B 2027/0123; G02B 2027/0132; G02B 2027/0178; G02B 26/0841; G02B 27/017; G02B 27/0172; G02B 5/008; G02B 5/30; G02B 6/00; G02B 6/0288; G02B 6/107; G02B 6/12; G02B 6/12009; G02B 6/12016; G02B 6/1226; G02B 6/14; G02B 6/2813; G02B 6/2817; G02B 6/29341; G02B 6/29344; G02B 6/421; G02B 6/4224; G02B 6/4226; G02B 6/4227; G01N 21/0303; G01N 2021/0346; G01N 21/05; G01N 21/59; G01N 21/645; G01N 21/6486; G01N 33/54373; G01N 33/551; G01N 2021/6484; G01N 21/554; G01N 21/6428; G01N 21/6454

See application file for complete search history.

(56) References Cited

U.S. PATENT DOCUMENTS

| | | | |
|---|---|---|---|
| 5,834,777 | A | 11/1998 | Wong |
| 6,324,329 | B1 | 11/2001 | Mizuno et al. |
| 6,694,067 | B1 | 2/2004 | O'Keefe et al. |
| 7,625,835 | B2 | 12/2009 | Li et al. |
| 7,683,005 | B2 | 3/2010 | Kurihara et al. |
| 7,778,499 | B2 | 8/2010 | Janz et al. |
| 8,135,246 | B2 | 3/2012 | Juni |
| 8,427,651 | B2 | 4/2013 | Digonnet |
| 8,503,849 | B2 * | 8/2013 | Decorby ............... G02B 6/1225 385/131 |
| 8,542,957 | B2 | 9/2013 | Yamashita et al. |
| 9,061,086 | B2 | 6/2015 | Morito et al. |
| 9,744,257 | B2 | 8/2017 | Lee et al. |
| 10,201,809 | B2 | 2/2019 | Ozaki et al. |
| 10,215,692 | B2 | 2/2019 | Tao et al. |
| 10,406,504 | B2 | 9/2019 | Kitazaki et al. |
| 10,434,505 | B1 | 10/2019 | Leung et al. |
| 10,598,590 | B2 | 3/2020 | Gylfason et al. |
| 10,604,733 | B2 | 3/2020 | Erickson et al. |
| 2003/0013304 | A1 * | 1/2003 | Deliwala ................. G02F 1/295 438/689 |
| 2006/0285114 | A1 * | 12/2006 | Cao .................... G01N 21/3504 356/437 |
| 2014/0056554 | A1 * | 2/2014 | Brunner .................. G02B 6/13 385/14 |

OTHER PUBLICATIONS

X. Mu et al, "Edge couplers in silicon photonic integrated circuits: a review," Appl. Sci. 2020, 10, 1538 (2020).

S. Suzuki et al, "Integrated-optic ring resonators with two stacked layers of silica waveguide on Si," IEEE Photonics Technology Letters, vol. 4, No. 11, pp. 1256-1258 (1992).

* cited by examiner

OPTICAL SENSING AND PHOTOCATALYSIS DEVICES BASED ON THREE-DIMENSIONAL WAVEGUIDING STRUCTURES AND METHOD OF USING SAME

FIELD OF THE INVENTION

The present embodiments generally relate to optical sensing and photocatalysis devices where at least one target substance interacts with light in a photonic integrated circuit (PIC). The target substance, which can be a gas or a liquid, is detected by the sensor or destroyed by the photocatalyst. The embodiments include at least one three-dimensional optical waveguiding PIC and operate with enhanced sensitivity and efficiency compared to prior art devices.

BACKGROUND

The optical sensing and photocatalysis devices described here utilize the interaction between (a) at least one target substance, (b) light at specific wavelength(s), and in the case of photocatalysis (c) a photocatalyst, at or in proximity to the device structures. A device can be used as a gas or liquid sensor by measuring the absorption level of the optical output due to the optical excitation of the target substance. It can also be used as a means of photocatalysis to convert undesirable organic materials such as a toxic gas or a virus into (i) a modified substance whose removal or destruction is more manageable, through the reactions with radicals created through oxidation and reduction of the undesirable materials or (ii) a third substance such as water. The prior art for gas sensing devices and the prior art for photocatalysis devices are described.

Out of several techniques used for gas sensing such as metal-oxide, electrochemical, catalytic beads, a nondispersive infrared (NDIR) sensor is attractive for potentially enhanced sensitivity and the ability to react specifically with the target substance. It is based on the emission of light with a specific wavelength into a target substance and measuring the absorption of the optical power. Since it operates at a specific wavelength where only a particular material has relatively high absorption, an NDIR sensor has the ability to specify the target substance as well. Unlike the cases of other gas sensors, an NDIR sensor has relatively long life time as well as a rapid response time because it is not subject to a chemical reaction. Further, since the measurement is based on photodetection, it generally has higher sensitivity than other types of sensors.

A sensor based on NDIR includes an optical emitter, a detector, and an optical waveguiding device. The absorption occurs when a target substance is present in the optical path between the emitter and the detector where the wavelength of the light matches at least one of the lines in the absorption spectrum of the target substance. As long as the specific wavelength has the absorption peaks dominantly at the target substance, the amount of the target substance can be measured based on the absorption level. In order to achieve a highly sensitive sensor so that the target substance can be detected even at low concentration, the waveguide is preferably designed to be long so that the amount of contact between the target substance and the waveguide is increased.

In prior art NDIR sensors, waveguides were used between the emitter and detector to guide emitted light to the detector while creating the contact area for the target substance to be measured. Wong (U.S. Pat. Nos. 5,444,249, 5,747,808, 5,834,777) describes sensors that are based on the integration of waveguides with a light source and a photodiode, and have a gas inlet. The advantages of using waveguide devices include small form factor and low cost. These waveguides include an under-cladding layer, a core layer, and at least one over-cladding layer on a substrate that is typically silicon. Since the waveguides in most cases are fabricated utilizing lithographic processes with a silicon substrate, the size of the waveguide chips is limited by the size of the substrate wafer and the number of chips patterned on each wafer, and this size is typically on the order of a square millimeter to a square centimeter. The small form factor in the prior art meant that a small area was available for the target substance to be in contact with the waveguide and to be measured.

In other prior art, improved waveguide structures were described for the realization of higher sensitivity devices. O'Keefe (U.S. Pat. No. 6,694,067) describes a waveguide with a pair of gratings that act as a cavity so that light is confined within the cavity for effectively longer propagation before reaching the detector. Janz (U.S. Pat. No. 7,778,499) describes a waveguide where the over-cladding layer was eliminated in order to enhance the relative amount of its spatial mode field in the air where the target substance is present. Digonnet (U.S. Pat. No. 8,427,651) describes a hollow core waveguide for the effective light confinement within air. Yamashita (U.S. Pat. No. 8,542,957), Tao (U.S. Ser. No. 10/215,692) and Gylfason (U.S. Ser. No. 10/598,590) describe waveguide structures with partial substrate removal so that sensing of the target substance can be achieved both from the top of the over-cladding and the bottom of the under-cladding. Although improved performance is expected in these prior art cases, the improvement is limited because it uses only a single waveguide layer.

Juni (U.S. Pat. No. 8,135,246) taught a sensor based on stacking a plurality of single-layer waveguide devices with a plurality of emitters and detectors. With the use of angular offset from the adjacent layer of a waveguide chip, the effective contact to the target substance can be achieved. However, this is an expensive method as the cost increases with the number of single-layer waveguide devices.

The present embodiments include the formation of photocatalysis devices. A photocatalysis device is a well-known device that absorbs a specific-wavelength light whose energy level is comparable to the bandgap of the device material, and generates an electron-hole pair that leads to a chemical reaction. For example, titanium dioxide absorbs ultraviolet (UV) light to generate an electron-hole pair which, in the presence of water and oxygen, generates radicals that react with and mineralize undesirable organic compounds, such as the lipid membranes that envelope and protect viruses such as Coronavirus Disease 2019 (COVID-19), allowing to pry apart the membranes and destroy the cells. In order for a photocatalytic device to be effective, the surface area where the photocatalyst (photocatalysis material) is exposed to said specific-wavelength light needs to be large.

Prior art by Kurihara (U.S. Pat. No. 7,683,005), Morito (U.S. Pat. No. 9,061,086), Lee (U.S. Pat. No. 9,744,257), Ozaki (U.S. Ser. No. 10/201,809), Kitazaki (U.S. Ser. No. 10/434,505) and Leung (U.S. Ser. No. 10/434,505) describe porous materials based on honeycomb structures, particles and fibers. The porous materials increase the effective surface area, however it works on a single surface so that the working area is limited by the area illuminated by said specific-wavelength light.

Mizuno (U.S. Pat. No. 6,324,329) and Li (U.S. Pat. No. 7,625,835) proposed waveguide structures where the outermost (over-cladding) layer comprises a photocatalytic material in order to create a photocatalytic effect. Said specific-wavelength light is guided inside their guiding layers as opposed to illuminating the surface of the photocatalytic material. In these cases, the illumination is not spatially limited. However, the photocatalytic reaction can only occur at one side of the surface as the waveguide structure is exposed to the target material only on one side. Erickson (U.S. Ser. No. 10/604,733) proposed a photocatalyst design with a plurality of waveguides with spaced relationship within the enclosure. In this case again, only the outermost layer of each waveguide comprises a photocatalytic material so that it reacts with the material within the same enclosure. This prior art can expect the efficiency increased with the plurality of waveguides. However, the spaced relationship within the enclosure limits the effective device size.

SUMMARY

The embodiments achieve enhanced sensitivity and efficiency of gaseous or liquid substance sensors and photocatalysts, by realizing three-dimensional waveguide structures that maximize the area of interaction between the substance and the sensing or photocatalysis device. The structure is preferably fabricated by the mature Complementary Metal-Oxide-Semiconductor (CMOS) process with a plurality of core layers within a chip. Each waveguiding layer is fabricated in such a way that the target gaseous or liquid substance can penetrate to where it can be illuminated with the light that propagates in the waveguide. Since the length of the waveguide scales with the number of layers, high-sensitivity sensors are designed with a plurality of layers. In surface-reacting devices for photocatalysis, an effective reaction is expected because the three-dimensional waveguide structure enhances the contact area without sacrificing the light intensity.

DESCRIPTION OF THE DRAWINGS

The following drawings are illustrative of the present embodiments and are not intended to limit the embodiments as encompassed by the claims forming part of the application.

The schematic diagram of FIG. 1 depicts prior art consisting of a single layer waveguide with its over-cladding layer exposed for improved overlap of light within the guided mode to the target gas in ambient air.

Figure 2:
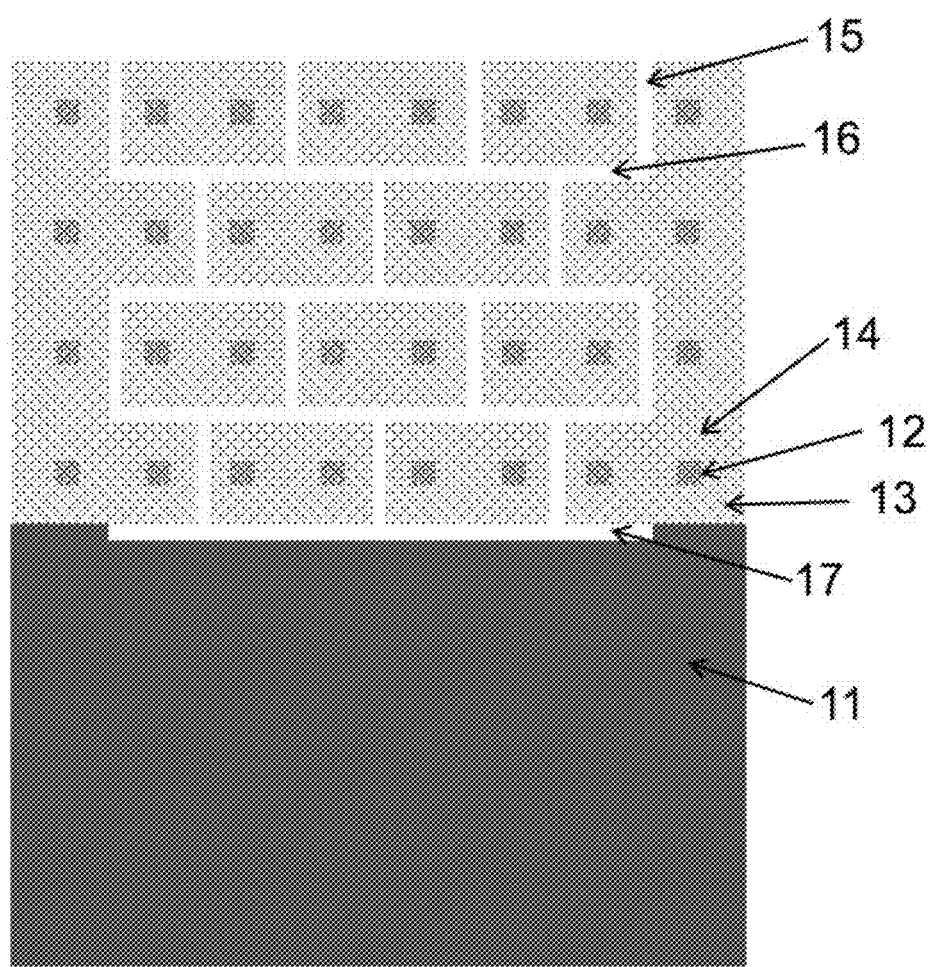

The schematic diagram of FIG. 2 depicts an embodiment consisting of a plurality of waveguiding layers with undercuts for each layer.

Figure 3:
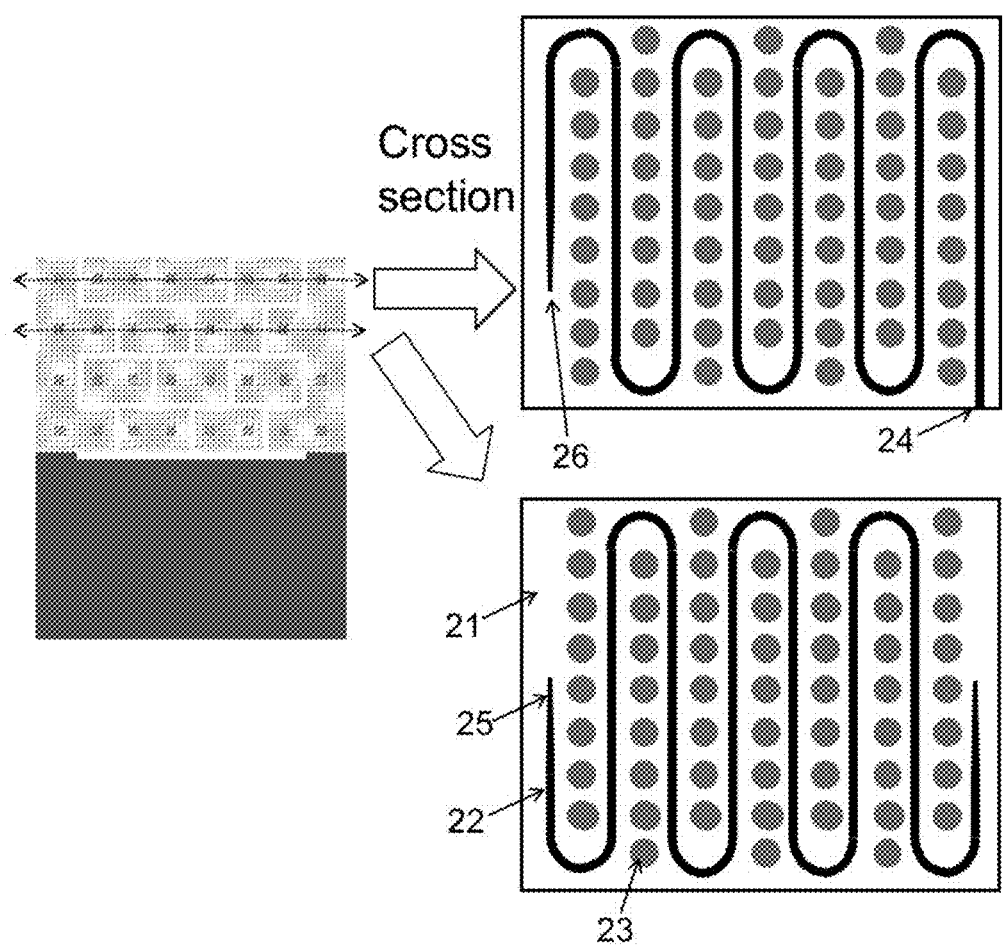

The schematic diagram of FIG. 3 depicts an embodiment of the waveguide design for different layers in the present embodiments.

Figure 4:
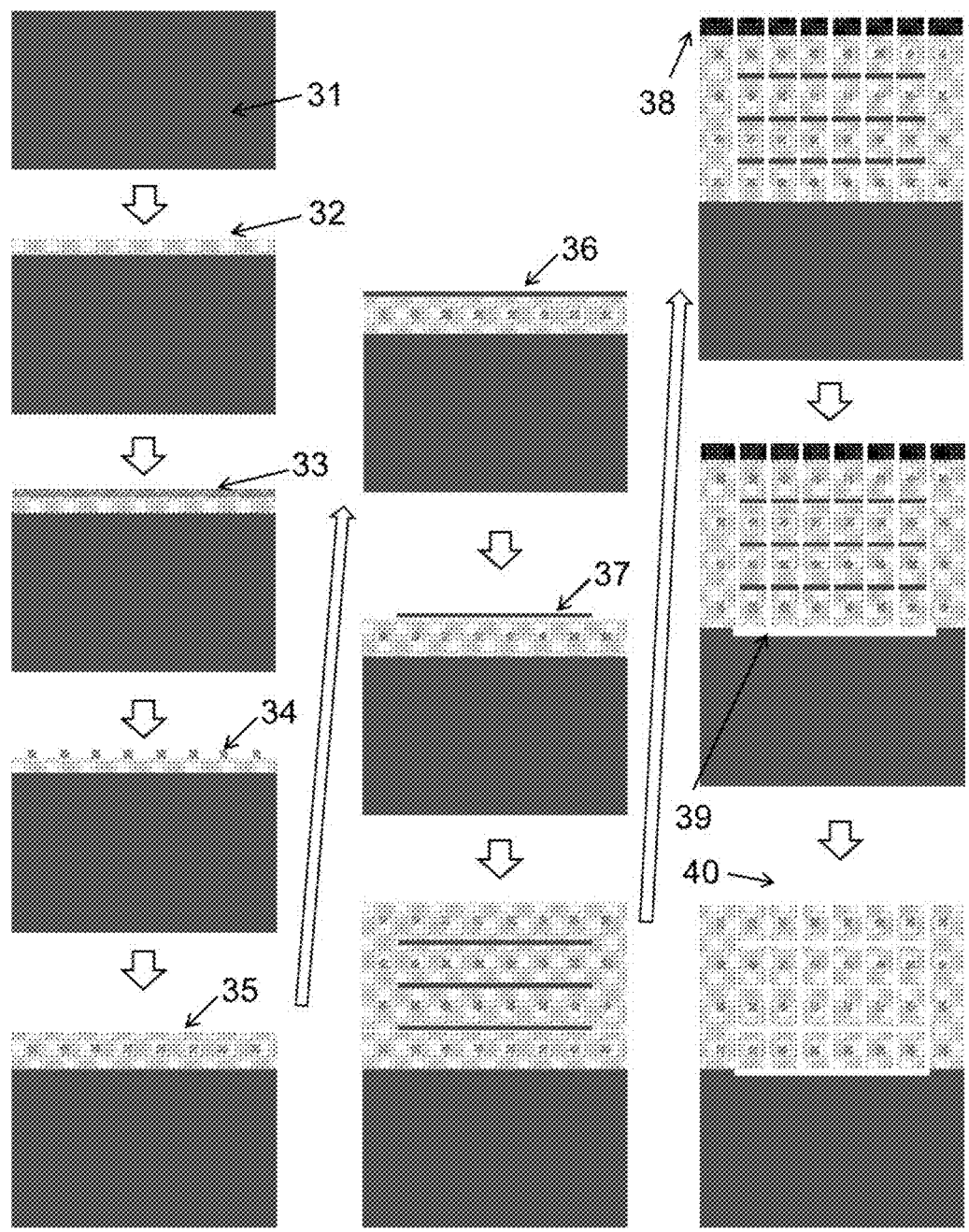

The schematic diagram of FIG. 4 depicts a first example of a method for fabricating the three-dimensional waveguide in the present embodiments.

Figure 5A:
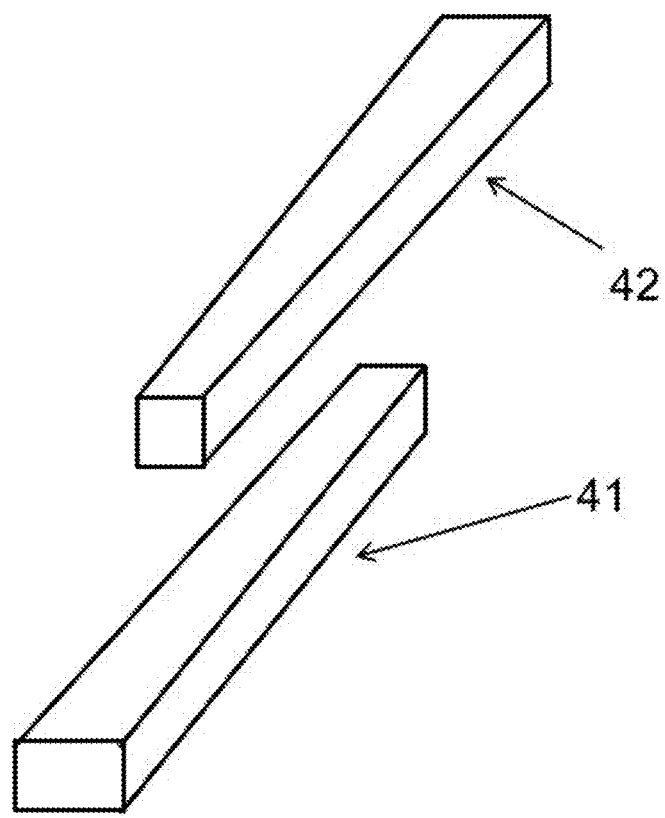

The schematic diagram of FIG. 5A depicts a three-dimensional view of an example of the vertical coupling design between waveguides in different layers.

Figure 5B:
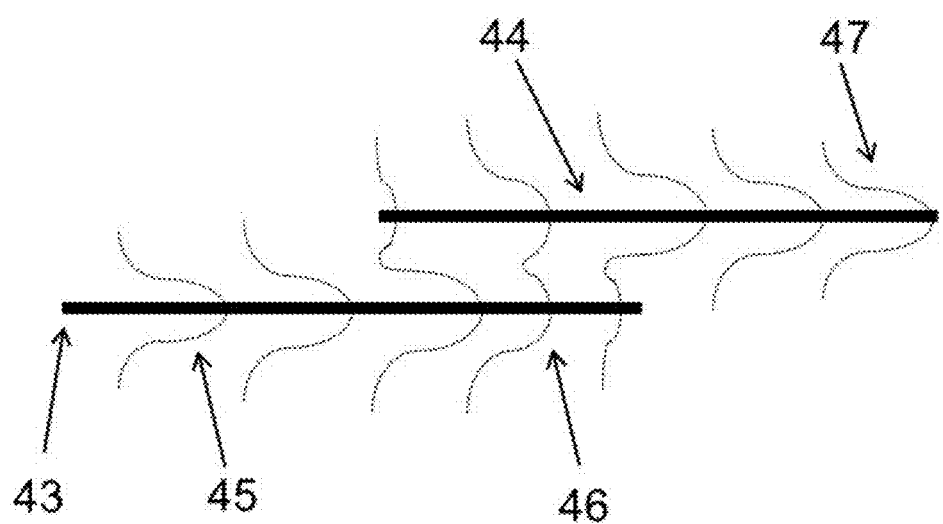

The schematic diagram of FIG. 5B depicts the side view of an example of the vertical coupling design between waveguides in different layers, and depicts the lightwave propagation within the waveguide coupler.

Figure 6:
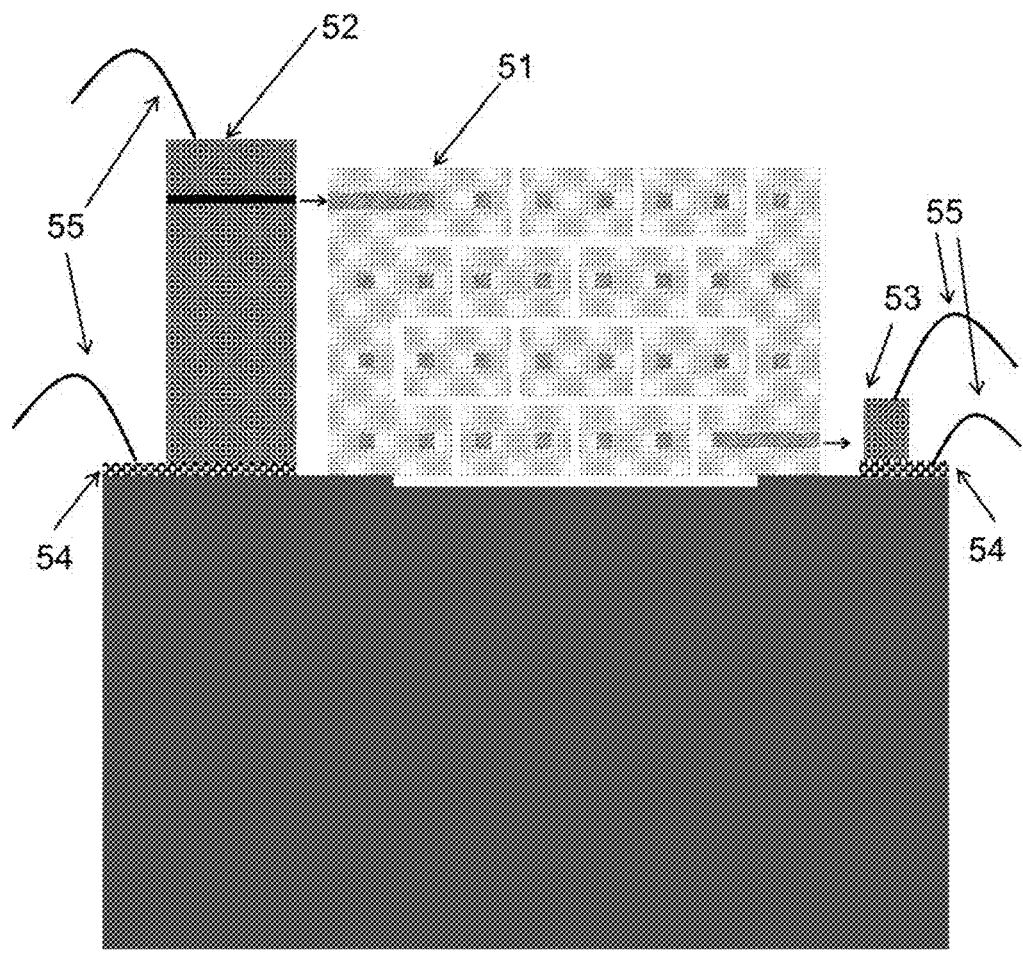

The schematic diagram of FIG. 6 depicts an embodiment of the integration of a laser and a photodiode on the substrate of the three-dimensional waveguide of the present embodiments.

Figure 7:
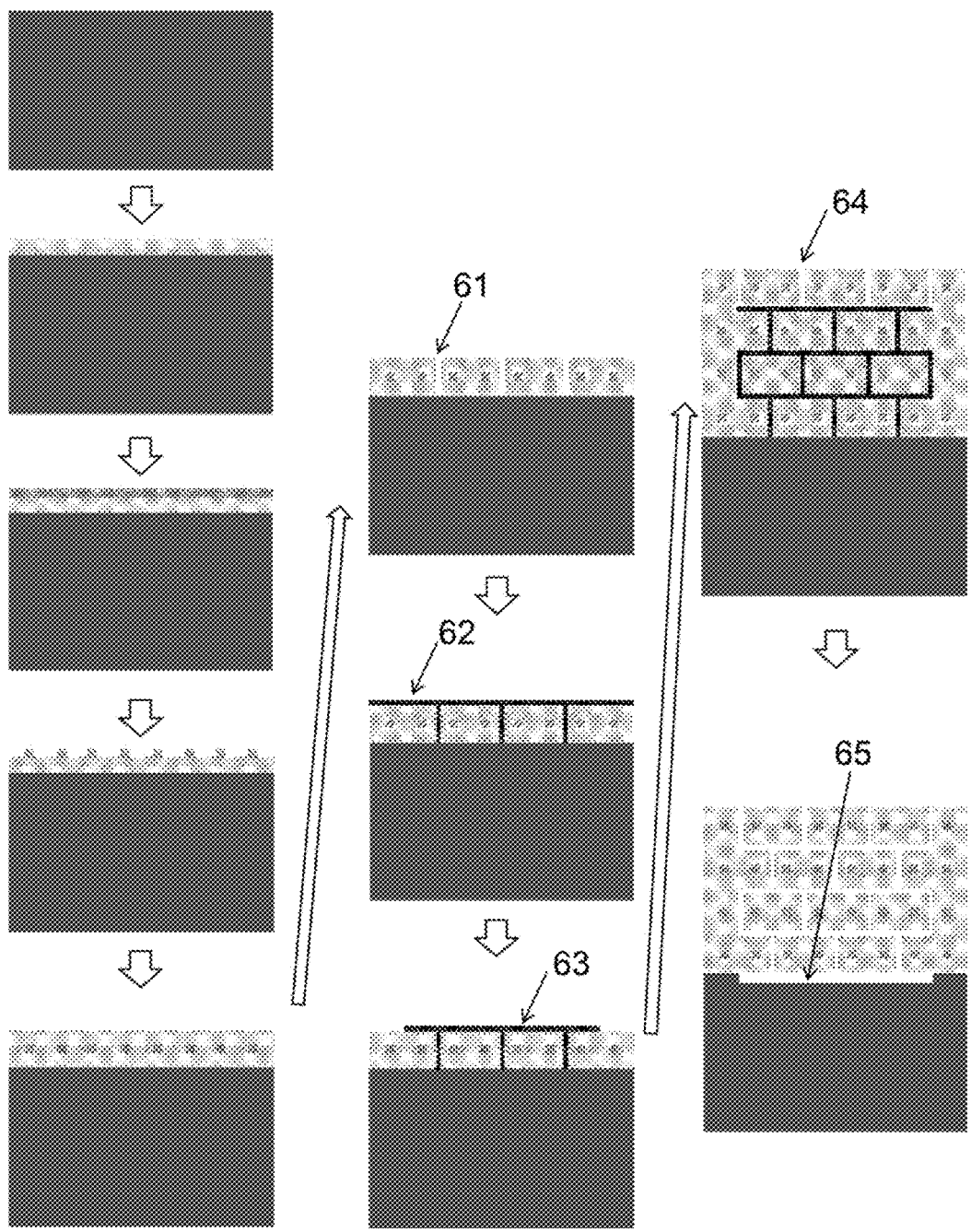

The schematic diagram of FIG. 7 depicts a second example of a method for fabricating the three-dimensional waveguide in the present embodiments.

DETAILED DESCRIPTION

It is known that an optical waveguide consists of a core and a cladding. The light is confined primarily in the core which is typically located at the center of the waveguide structure and has refractive index that is larger than that of the cladding. The confinement level depends on the difference in the refractive indices between the core and the cladding. The larger difference in the refractive indices, the tighter the light confinement within the core. For a typical waveguide structure, cladding layers exist both underneath the core (under-cladding) and above the core (over-cladding). The cladding on the sides of the core is typically part of the over-cladding.

Figure 1:
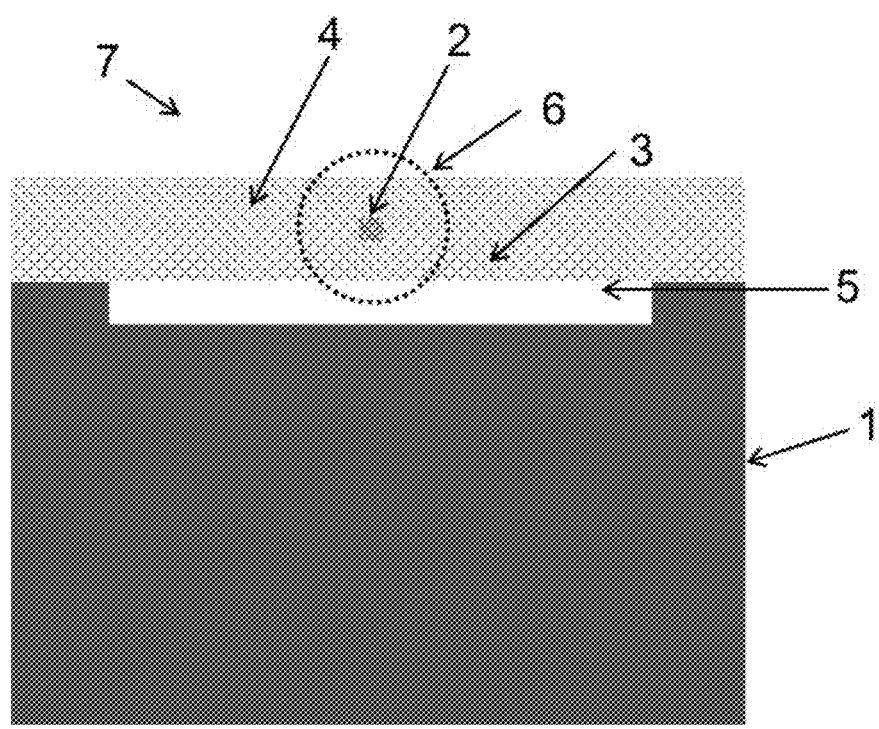

For sensing applications, the waveguides have sensing regions where the target gaseous or liquid substance penetrates and can be sensed. In many cases, the waveguides are designed to have air underneath the under-cladding and/or on top of the over-cladding so that the specific substance can enter and interact with the guided light. In addition, the waveguide is preferably designed with loose optical confinement so that a relatively large portion of the guided spatial mode(s) of the waveguide extends into the air (air is used here as example, the environment can be any gas or liquid) outside the device. The target substance can be detected by the portion of the guided mode extending into the air. FIG. 1 depicts the basic structure of waveguide-based sensors based on prior art by Wong (U.S. Pat. Nos. 5,444,249, 5,747,808, 5,834,777), O'Keefe (U.S. Pat. No. 6,694,067), Janz (U.S. Pat. No. 7,778,499), Digonnet (U.S. Pat. No. 8,427,651), Yamashita (U.S. Pat. No. 8,542,957), Tao (U.S. Ser. No. 10/215,692) and Gylfason (U.S. Ser. No. 10/598,590). FIG. 1 has been simplified to remove details of each prior art reference that are irrelevant to the concept of the present embodiments. The basic structure represented schematically in FIG. 1 has either substrate, 1, or other means to mechanically support a waveguide. On top of the substrate, it has a waveguide core, 2, under-cladding layer, 3, and over-cladding layer, 4. It may also include an undercut of the substrate, 5, underneath the under-cladding. The waveguide has a spatial optical mode, 6, that at least partially extends into the region where the target substance may exist. In most cases, when the target substance is present in the surrounding environment, it would be present above the over-cladding, 7, and/or in the substrate undercut, 5. The exposure of the waveguide mode to the target substance causes light absorption, allowing the concentration of the target substance to be identified by measuring the output power of the light that propagates in the waveguide. Prior art references attempt to improve the sensitivity of the detection by increasing the relative amount of the guided mode to the region where the target substance may exist. However, the improvement is limited due to the fact that it only has a single waveguiding layer consisting of core and claddings.

Enhancement of the sensitivity can be achieved by stacking such single-layer devices, as proposed by Juni (U.S. Pat. No. 8,135,246). However, Juni's design requires a plurality of waveguide devices (each having its own unique substrate), a plurality of emitters, a plurality of photodiodes, and an increase in the size, power consumption, and cost of the full sensor, all of which scale with the number of waveguide devices, emitters, and photodiodes.

The present embodiments achieve the enhanced sensitivity of an optical sensor that interacts with a target substance through the fabrication and use of a multi-layer waveguide device that has a minimal increase in the chip size and cost compared to the single-layer counterpart. Device designs with a plurality of cores already exist. For example, a multi-core fiber has been proposed and fabricated, such as described by Imamura, to transport a plurality of optical signals in parallel. In a planar waveguide structure, the multi-layer structure has been used primarily for coupling between waveguides of different materials, as described by Mu, and same materials, as described by Suzuki. However, no prior art describes a device based on a plurality of waveguiding layers on the same substrate, for maximizing the interaction with an external substance as needed in a sensitive sensor and an efficient photocatalyst, and doing so in a manner that minimizes the size, power consumption, and cost.

The sensing device based on an embodiment of the three-dimensional waveguide of the present embodiments is depicted schematically in FIG. 2. It consists of a substrate, 11, and a plurality of waveguiding layers where each layer consists of a core, 12, an under-cladding, 13, and an over-cladding, 14. It also has an opening region consisting of through holes, 15, as well as undercuts at the boundaries between two layers, 16, and an undercut at the top of the substrate, 17. The target substance has access to all the through holes and undercuts so that it can be sensed by the waveguides at all layers. The design based on the present embodiments is based on photonics integrated circuits (PIC's) which can be fabricated by the mature Complementary Metal-Oxide-Semiconductor (CMOS) process.

FIG. 3 depicts schematically the cross section of an embodiment of the three-dimensional waveguide of the present embodiments. Each waveguiding layer, 21, consists of at least one waveguide, 22, and through holes, 23, as described earlier. The design of waveguides and holes may be layer-dependent. The waveguiding structure needs to have at least one input and one output, 24, where the light can be coupled from an external emitter (at input) and can be measured by an external photodetector (at output). In general, the waveguide is designed to be long in order to maximize the interaction between the guided mode to the target substance. In order to maximize the waveguide length, the device may have at least one vertical coupling region, 25, and its mating vertical coupling at the adjacent layer, 26, so that the guided light can propagate from one layer to the other.

One example of realizing a sensor with a plurality of core layers is depicted schematically in FIG. 4 and is as follows: on a preferably silicon substrate, 31, the under-cladding layer, 32, and core layer, 33 are deposited sequentially. After the core deposition, the core waveguide structure, 34, is created by lithography and subsequent etching. After the deposition of the over-cladding layer, 35, to complete the first waveguiding layer (the multi-layer stack related to one core layer), a sacrificial layer, 36 is deposited and is patterned, 37. The process of depositing and patterning of waveguiding layers (which include sacrificial layers except for the last layer) is repeated for the design number of waveguiding layers. After the deposition of all layers, the opening structures are created by depositing and patterning a mask layer 38, which can be photoresist or a material patterned using photoresist. The openings are positioned in locations that do not have waveguide cores underneath. The opening features are preferably etched all the way to the bottom of the entire layer stack (i.e., to the top of the substrate). The etching of the opening structures, 38, is performed so that the verticality of the patterned area is maintained. Subsequent wet etching removes the sacrificial layer and creates an undercut, 39, at the top of the substrate. Lastly, the patterning for the opening structures is removed. The final structure, 40, includes a plurality of waveguiding layers (under-cladding, core, and over-cladding) where most of the waveguide has air both underneath the under-cladding and above the over-cladding, allowing the target substance to reach any of the waveguiding layers.

For sensing applications, the waveguide core within each waveguiding layer is routed to preferably maximize the core length while leaving space for openings. Also, at the extremity of the waveguide core within a layer, a vertical coupling structure can be created. The vertical coupling is achieved by overlapping the spatial modes of adjacent layers, and can be enhanced by designing the waveguide geometry at coupling extremities in adjacent layers to decrease the mode confinement, thereby increasing the size of modes in adjacent layers and the spatial overlap between said modes. The coupling length is chosen for efficient coupling between the two vertical layers (i.e., coupling of optical power from one layer to another in a short distance). One example of a vertical coupling structure is depicted schematically in FIG. 5A. The waveguides of the two layers are designed to propagate along the same in-plane axis and are terminated with tapered core structures, 41 and 42. FIG. 5B depicts schematically the mode propagation within the two waveguides, 43 and 44. The mode of the bottom layer, 45, is enlarged with the tapered waveguide core and gradually couples to the waveguide core of the top layer, 46. The length of the coupling region is designed so that the spatial mode, 47, at the end of the tapered structure in the first layer (the layer that initially has most of the optical power) is predominantly located at the guiding region of the top layer. This way the optical power was transferred from one layer to the adjacent vertical layer. The same process can be repeated, allowing light to propagate throughout the three-dimensional waveguiding structure, thereby substantially increasing the length of the optical waveguide, thus substantially enhancing the sensitivity of the sensor.

In many cases, a reference waveguide that does not interact with the substance of interest is fabricated on the same substrate in order to compare the output power with and without the presence of said substance. The reference waveguide can be implemented onto the same chip by partially splitting light from the emitter and guiding the light directly to a photodiode with essentially no exposure to the surrounding environment and its substances.

The light from the emitter can be coupled into the input of the three-dimensional waveguide and the reference waveguide by lens, fiber, grating, diffractive optical element (DOE), or butt-coupling. The photodiodes for the sensor waveguide and the reference waveguides can also be butt-coupled as well as coupled with lens, fiber, grating, or DOE. Alternatively, emitter and photodiode can be integrated within the three-dimensional waveguide device, as depicted schematically in FIG. 6. For the three-dimensional waveguide chip, 51, the laser, 52, and the photodiode, 53, are mounted on metal pads, 54. The electrical connection to the control board is typically made using wire bonds, 55. The integration of the emitter and the photodiode on the same substrate as the waveguiding structure further reduces the overall size and cost, as well as enhances the stability and reliability of the device.

The first example of the sensor is relatively easy to be fabricated. However, it may not be optimal because the opening structures go all the way from the top to the bottom of the multi-layer stack. With such a design, the target substance may flow away from the sensor without distributing uniformly within the entire chip. The second example, as depicted schematically in FIG. 7, is designed to position the openings so that each opening does not penetrate all the way from the top to the bottom of the multi-layer stack. In this design, the target substance is more likely to uniformly contact the majority of the waveguide layers.

For the second example, the fabrication of the under-cladding, core, and over-cladding of the first waveguiding layer is performed in the same way as in the first example. After the deposition of the first waveguiding layer, opening structures, 61, are patterned and etched. After fabricating the opening structures in each waveguiding layer, a sacrificial layer is deposited, 62, and patterned, 63. This process from the deposition of under-cladding to the patterned sacrificial layer is repeated for the plurality of waveguiding layers, except that the top waveguiding layer, 64, does not have a sacrificial layer. After the deposition of all layers, wet etching is performed to remove the patterned sacrificial layers as well as to create an undercut at the top of the substrate, 65. The opening pattern for each waveguide layer is designed so that the substance can effectively flow and make contact within the entire three-dimensional waveguide structure.

The two examples described are designed to maximize the waveguide length and therefore enhance the sensitivity of the sensor. Another advantage of the three-dimensional waveguide structure is that it affords the space to make multiple measurements with different waveguide lengths. Obtaining waveguide-length-dependent absorption data leads to higher accuracy in the measurement. In one embodiment, each layer can have a different waveguide length, and a photodiode can be used for each layer. Light is input in each layer. The output of one light source can be split (e.g., by having a light source with a broad spatial beam), or a light source can be used for each layer or for a few layers.

The present embodiments can be applied to a photocatalysis device. The device can be fabricated in a manner substantially similar to the second example of the substance sensing device. However, unlike the sensor case of the present embodiments, the waveguide structure needs to include photocatalytic material (such as titanium dioxide) that is exposed in areas where it can be in contact with the target substance. One way to achieve this is to use a photocatalytic material in the over-cladding and/or under-cladding. Another way to achieve this is to use a photocatalytic material as the core of waveguide and remove at least portion of the over-cladding and/or under-cladding. Another difference of the waveguide structure from the case of the substance sensing device is that the optical measurement is not needed. This means that the photocatalytic device does not require a photodetector or a waveguide design with pre-determined length. Each waveguide may be terminated within the same layer without any vertical coupling. The waveguide design may include a splitter to split the power into a plurality of waveguides. The light source of the present embodiments for photocatalytic devices needs to be selected so that (1) it operates at the wavelength that generates the photocatalytic effect and (2) it couples light into all waveguides by (a) being constituted of a plurality of light sources, (b) generating multiple beams, or (c) emitting a large beam to cover all the locations of waveguide inputs.

In terms of the multilayer approach to maximize the area of the photocatalytic effect, the present embodiments differ from all prior art except Erickson. Unlike the case of Erickson, the waveguide for each layer can be routed freely within the layer, regardless of how the waveguides of other layers are routed, to maximize the area with photocatalytic effect. The number of waveguides within each layer can be modified, such as with splitters, to increase the density of waveguides. Therefore, one can design a photocatalyst with a proper chip size depending on the amount of target materials to be removed.

A further embodiment comprises an air flow system designed to circulate the air in an essentially confined space (e.g., room, office, restaurant, factory) through one or multiple photocatalysis devices described in these embodiments, thereby purifying and/or disinfecting the air. Contaminants removed from the air and destroyed include virus cells such as Coronavirus Disease 2019 (COVID-19).

What is claimed is:
1. A photoreaction device comprising:
   a. At least one light source that can react with a target substance;
   b. A three-dimensional optical waveguiding structure based on a plurality of waveguiding layers on a substrate where a waveguiding pattern within each layer is designed independently;
   c. At least one cavity that runs in proximity to at least a portion of said waveguiding structure, constituting the area that a target gaseous or liquid substance enters, said substance overlapping at least partially with the spatial optical mode of said waveguiding structure;
   and wherein light from said at least one light source is coupled into the at least one input of said three-dimensional optical waveguiding structure and propagates within said plurality of waveguiding layers to achieve a photo-induced reaction with a target substance.

2. The photoreaction device of claim 1 wherein said light source is integrated on the substrate of said three-dimensional waveguiding structure.

3. The photoreaction device of claim 1 wherein at least one of said waveguiding layers comprises an optical splitter that splits the waveguide in the waveguiding layer into a plurality of waveguides.

4. The photoreaction device of claim 1 wherein the surface of at least a portion of said at least one cavity comprises a photocatalytic material, thereby making the device a photocatalysis device.

5. The photocatalysis device of claim 4 wherein said photocatalytic material is titanium dioxide.

6. The photocatalysis device of claim 5 wherein the at least one light source emits ultraviolet light.

7. A least one photocatalysis device of claim 4 comprised in an air flow system designed to circulate the air in an essentially confined space through said at least one photocatalysis device.

8. The air flow system of claim 7 designed to remove impurities from the air.

9. The air flow system of claim 8 designed to disinfect the air of particular harmful cells, thereby making the system a disinfection system.

10. The disinfection system of claim 9 wherein the particular harmful cells include viruses protected by lipid membranes.

11. The disinfection system of claim 10 wherein said viruses are coronavirus cells.

12. The disinfection system of claim 11 wherein said coronavirus cells are Coronavirus Disease 2019 (COVID-19) cells.

13. A substance sensing device comprising:
   a. At least one light source that can be absorbed by a target substance;
   b. At least one photodetector;
   c. A three-dimensional optical waveguiding structure based on a plurality of waveguiding layers on a substrate where a waveguiding pattern within each layer is designed independently;
   d. At least one cavity that runs in proximity to at least a portion of said waveguiding structure, constituting the area that a target gaseous or liquid substance enters, said substance overlapping at least partially with the spatial optical mode of said waveguiding structure;
   and wherein light from said at least one light source is coupled into said three-dimensional optical waveguiding structure and propagates within said structure until impinging on said at least one photodetector, having travelled through and been attenuated by said target substance.

14. The substance sensing device of claim 13 wherein at least a pair of the plurality of waveguiding layers have coupling structures that transfer light from one layer to the other.

15. The substance sensing device of claim 13 wherein said coupling structures are mirrors.

16. The substance sensing device of claim 13 wherein said coupling structures are gratings.

17. The substance sensing device of claim 13 wherein said at least one light source is integrated on the substrate of said three-dimensional optical waveguiding structure.

18. The substance sensing device of claim 13 wherein said at least one photodetector is integrated on the substrate of said three-dimensional optical waveguiding structure.

19. The substance sensing device of claim 13 further including:
   a reference waveguide that is distant from said cavity and wherein light propagates essentially without being absorbed by the target substance.

20. A method for a photoreaction device, comprising:
   a. Guiding light, from at least one light source, in a three-dimensional optical waveguiding structure based on a plurality of waveguiding layers on a substrate where a waveguiding pattern within each layer is designed independently;
   b. Illuminating with said at least one light source, in at least one cavity that runs in proximity to at least a portion of said waveguiding structure, a target gaseous or liquid substance, and achieve a photo-induced reaction with said target substance.

21. A method for a photocatalysis device, comprising:
   a. Guiding light, from at least one light source, in a three-dimensional optical waveguiding structure based on a plurality of waveguiding layers on a substrate where a waveguiding pattern within each layer is designed independently;
   b. Illuminating with said at least one light source, in at least one cavity that runs in proximity to at least a portion of said waveguiding structure, a target gaseous or liquid substance;
   c. Photocatalyzing said target substance, via a photocatalytic material included in the surface of at least a portion of said at least one cavity.

* * * * *